(12) United States Patent
Katakura

(10) Patent No.: US 8,531,511 B2
(45) Date of Patent: Sep. 10, 2013

(54) DIFFRACTIVE OPTICAL ELEMENT AND ENDOSCOPE

(71) Applicant: Olympus Medical Systems Corp., Tokyo (JP)

(72) Inventor: Masahiro Katakura, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/633,522

(22) Filed: Oct. 2, 2012

(65) Prior Publication Data

US 2013/0070070 A1  Mar. 21, 2013

Related U.S. Application Data

(63) Continuation of application No. PCT/JP2012/053096, filed on Feb. 10, 2012.

(30) Foreign Application Priority Data

Mar. 18, 2011  (JP) .................................. 2011-061320

(51) Int. Cl.
  *H04N 7/18*  (2006.01)
(52) U.S. Cl.
  USPC ................ 348/65; 348/61; 359/576; 359/575
(58) Field of Classification Search
  USPC ..................................................... 348/61, 65
  See application file for complete search history.

(56) References Cited

U.S. PATENT DOCUMENTS

| | | | | |
|---|---|---|---|---|
| 7,236,302 B2 * | 6/2007 | Nakai et al. | ..................... | 359/571 |
| 7,710,651 B2 * | 5/2010 | Yasui | ............................. | 359/576 |
| 7,829,326 B2 * | 11/2010 | Norman | ..................... | 435/287.1 |
| 2002/0163725 A1 * | 11/2002 | Kobayashi | ..................... | 359/569 |
| 2006/0171031 A1 | 8/2006 | Suzuki | | |
| 2007/0230311 A1 | 10/2007 | Kawakita et al. | | |
| 2008/0019001 A1 | 1/2008 | Suzuki | | |
| 2008/0231956 A1 | 9/2008 | Yasui | | |
| 2009/0168205 A1 | 7/2009 | Inoue | | |
| 2009/0190224 A1 | 7/2009 | Iwasa | | |

FOREIGN PATENT DOCUMENTS

| | | |
|---|---|---|
| JP | 02-179605 | 7/1990 |
| JP | 11-271513 | 10/1999 |
| JP | 11-287904 | 10/1999 |
| JP | 2005-107298 | 4/2005 |
| JP | 2007-273012 | 10/2007 |

(Continued)

OTHER PUBLICATIONS

International Search Report, dated May 22, 2012, issued in corresponding International Application No. PCT/JP2012/053096.

*Primary Examiner* — Jay Patel
*Assistant Examiner* — Jessica Prince
(74) *Attorney, Agent, or Firm* — Kenyon & Kenyon LLP

(57) ABSTRACT

Provided is a diffractive optical element that is formed by laminating two optical material layers formed of different energy-cured resins; in which a relief pattern is formed at the interface between the two optical material layers; and that satisfies the following conditional expressions:

$$0.01 < d_2/d_1 < 0.2 \tag{1}$$

$$0.05 < d_1/\phi E < 1.0 \tag{2}$$

$$0.0005 < d_2/\phi E < 0.1 \tag{3}$$

wherein $d_1$ is the center plate thickness (mm) of one optical material layer 2 that is cured first, $d_2$ is the center plate thickness (mm) of the other optical material layer 3 that is cured later, and $\phi E$ is the effective diameter (mm) of the relief pattern 4.

20 Claims, 3 Drawing Sheets

(56) References Cited

FOREIGN PATENT DOCUMENTS

| | | |
|---|---|---|
| JP | 2008-026440 | 2/2008 |
| JP | 2008-242391 | 10/2008 |
| JP | 2009-197217 | 9/2009 |
| WO | 2007/111077 | 10/2007 |
| WO | 2009/096389 | 8/2009 |
| WO | 2011/136015 | 11/2011 |

* cited by examiner

DIFFRACTIVE OPTICAL ELEMENT AND ENDOSCOPE

CROSS-REFERENCE TO RELATED APPLICATIONS

This is a continuation of International Application PCT/JP2012/053096, with an international filing date of Feb. 10, 2012, which is hereby incorporated by reference herein in its entirety. This application claims the benefit of Japanese Patent Application No. 2011-061320, the content of which is incorporated herein by reference.

TECHNICAL FIELD

The present invention relates to a diffractive optical element and an endoscope.

BACKGROUND ART

In the related art, due to their ability to well-correct the chromatic aberrations in optical systems, diffractive optical elements have been disclosed in many publications below (for example, see Patent Literatures 1 to 7).

CITATION LIST

Patent Literature

{PTL 1} Japanese Unexamined Patent Application, Publication No. Hei 2-179605
{PTL 2} Japanese Unexamined Patent Application, Publication No. Hei 11-271513
{PTL 3} Japanese Unexamined Patent Application, Publication No. Hei 11-287904
{PTL 4} Japanese Unexamined Patent Application, Publication No. 2007-273012
{PTL 5} Japanese Unexamined Patent Application, Publication No. 2009-197217
{PTL 6} Japanese Unexamined Patent Application, Publication No. 2005-107298
{PTL 7} PCT International Publication No. WO 2007/111077

SUMMARY OF INVENTION

Technical Problem

Because the diffractive optical element disclosed in Patent Literature 1 is not laminated, the diffraction efficiency thereof strongly depends on wavelength, and this causes flare when installed in an endoscope (flexible scope or rigid scope), contrary to the intended effect thereof.

Also, in the diffractive optical elements disclosed in Patent Literatures 2 and 3, optical elements in which relief patterns are formed are laminated. By doing so, a high diffraction efficiency can be achieved for first-order diffracted beams (hereinafter, referred to simply as diffraction efficiency) in a wide wavelength range; however, there is a problem in that, because one of the two layers of the optical elements is made of a glass material, processing the relief pattern therein is difficult, they are difficult to mass produce, and they are also expensive.

Furthermore, because the diffractive optical elements disclosed in Patent Literatures 4 to 7 are made of resins, they have excellent processability and are easy to mass produce, and they can be manufactured at a low-cost; however, conditions for the mid-plate thickness are not appropriately set which makes warping and separation during the manufacturing processes more likely.

Solution to Problem

A first aspect of the present invention provides a diffractive optical element that is formed by laminating two optical material layers formed of different energy-cured resins; in which a relief pattern is formed at an interface between the two optical material layers; and that satisfies the following conditional expressions:

$$0.01 < d_2/d_1 < 0.2 \tag{1}$$

$$0.05 < d_1/\phi E < 1.0 \tag{2}$$

$$0.0005 < d_2/\phi E < 0.1 \tag{3}$$

wherein $d_1$ is the center plate thickness (mm) of one optical material layer that is cured first, $d_2$ is the center plate thickness (mm) of the other optical material layer that is cured later, and $\phi E$ is the effective diameter (mm) of a relief pattern.

A second aspect of the present invention provides an endoscope provided with the diffractive optical element described above.

DESCRIPTION OF EMBODIMENTS

A diffractive optical element according to an embodiment of the present invention will be described below with reference to the drawings.

Figure 1:
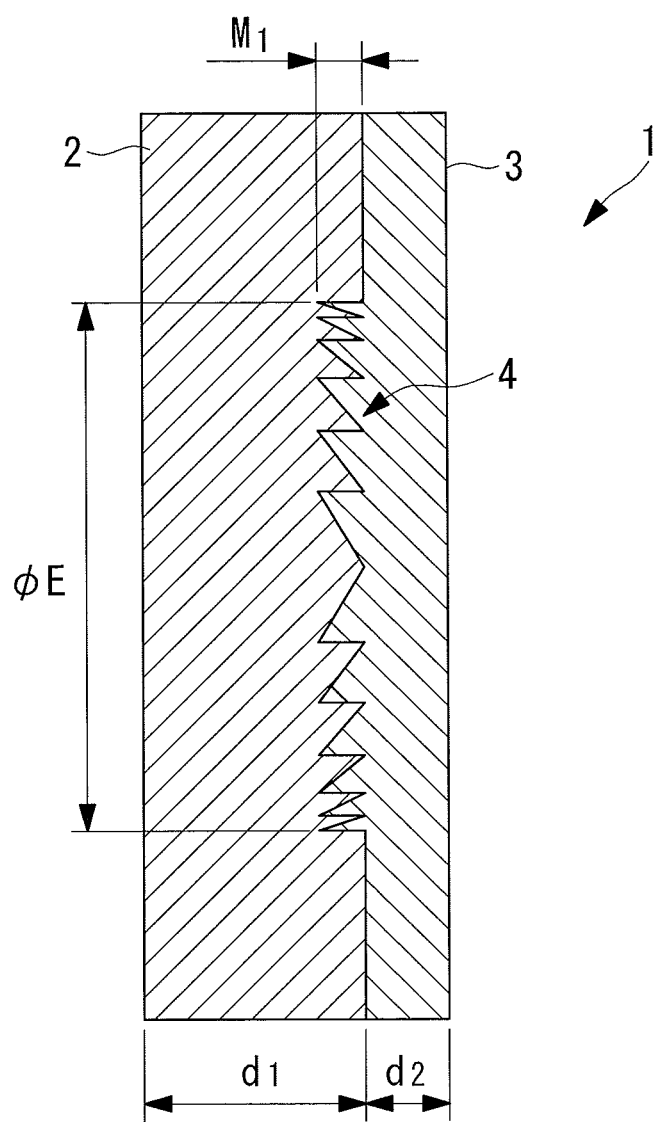
FIG. 1 is a longitudinal sectional view of a diffractive optical element according to an embodiment of the present invention.

As shown in FIG. 1, a diffractive optical element 1 according to this embodiment is a multilayer diffractive optical element 1 in which a first optical material layer 2 and a second optical material layer 3 are laminated.

The two optical material layers 2 and 3 are formed of different energy-cured resins.

The first optical material layer 2 is an optical material layer that is cured first, whose center plate thickness is $d_1$, whose refractive index at the d-line is $n_1$, and whose Abbe number is $v_1$. The second optical material layer 3 is an optical material layer that is cured later, whose center plate thickness is $d_2$, whose refractive index at d-line is $n_2$, and whose Abbe number is $v_2$.

In addition, a relief pattern 4 is formed at the interface between the first optical material layer 2 and the second optical material layer 3. The relief pattern 4 has irregularities whose pitch gradually decreases radially outward from the center. The depth $M_1$ of the relief pattern 4 is nearly uniform over the entire relief pattern 4, and the effective diameter of the relief pattern 4 is $\phi E$.

Then, in this embodiment, the following conditional expressions are satisfied.

$$0.01 < d_2/d_1 < 0.2 \quad (1)$$

$$0.05 < d_1/\phi E < 1.0 \quad (2)$$

$$0.0005 < d_2/\phi E < 0.1 \quad (3)$$

$$1.5 < n_1 < 1.8 \quad (4)$$

$$1.5 < n_2 < 1.8 \quad (5)$$

$$10 < \nu_1 < 50 \quad (6)$$

$$10 < \nu_2 < 50 \quad (7)$$

$$0.8 < M_1 \times |n_1 - n_2|/\lambda d < 1.2 \quad (8)$$

$$0.0001 < |n_1 - n_2| < 0.4 \quad (9)$$

$$0 < |\nu_1 - \nu_2| < 30 \quad (10)$$

wherein λd is the wavelength at the d-line.

The thus-configured diffractive optical element 1 according to this embodiment affords the following advantages.

By laminating the two optical material layers 2 and 3, the diffraction efficiency can be increased in the wavelength range used.

In addition, by forming the two optical material layers 2 and 3 with energy-cured resins, the processability and mass-productivity can be enhanced, and a cost reduction can be achieved.

Furthermore, by forming the relief pattern 4 at the interface between the two optical material layers 2 and 3, a diffractive optical element 1 that has a focusing effect like a lens can be manufactured.

In this case, by satisfying conditional expression (1), the ratio of the mid-plate thicknesses between the optical material layer 2, which is cured first, and the optical material layer 3, which is cured later, is set to be an appropriate ratio, and thus, warping and separation of the optical material layers 2 and 3 can be reduced.

If the upper limit of conditional expression (1) is exceeded, the mid-plate thickness of the optical material layer 3 that is cured later becomes too large, which generates a large stress, making warping and separation more likely. On the other hand, if the lower limit of conditional expression (1) is exceeded, the mid-plate thickness of the optical material layer 3 that is cured later becomes too small, which decreases the processability and the mass-productivity.

In addition, by satisfying conditional expressions (2) and (3), the ratio of the mid-plate thicknesses is appropriately set and warping and separation become less likely. If the upper limits of conditional expressions (2) and (3) are exceeded, because the mid-plate thicknesses of the optical material layers 2 and 3 become too large, which generates a large stress, warping and separation become more likely. If the lower limits of conditional expressions (2) and (3) are exceeded, the mid-plate thicknesses of the optical materials 2 and 3 become too small, which decreases the processability and the ease of mass production.

In addition, by satisfying conditional expressions (4), (5), (6), and (7), the energy-cured resins that form the optical material layers 2 and 3 can be procured.

Furthermore, by satisfying conditional expression (8), the groove depth is appropriately set, which allows manufacturing of a diffractive optical element 1 having a high diffraction efficiency in a wide wavelength range. If conditional expression (8) is not satisfied, the wavelength range in which a high diffraction efficiency is achieved becomes narrower.

In addition, by satisfying conditional expression (9), the refractive index difference of the energy-cured resins that form the optical material layers 2 and 3 is appropriately set. If the upper limit of the conditional expression (9) is exceeded, procurement of the energy-cured resins becomes considerably difficult. If the lower limit of conditional expression (9) is exceeded, the groove depth $M_1$ becomes too deep, which makes processing considerably difficult.

Furthermore, by satisfying conditional expression (10), the Abbe number difference of the energy-cured resins that form the optical material layers 2 and 3 is appropriately set. If conditional expression (10) is not satisfied, procurement of the energy-cured resins becomes considerably difficult.

Note that, in this embodiment, it is preferable that the following conditional expressions (1'), (2'), and (3') be satisfied instead of conditional expressions (1), (2), and (3), and it is further preferable that conditional expressions (1"), (2"), and (3") be satisfied.

$$0.03 < d_2/d_1 < 0.15 \quad (1')$$

$$0.07 < d_1/\phi E < 0.6 \quad (2')$$

$$0.0007 < d_2/\phi E < 0.06 \quad (3')$$

$$0.05 < d_2/d_1 < 0.12 \quad (1'')$$

$$0.1 < d_1/\phi E < 0.4 \quad (2'')$$

$$0.001 < d_2/\phi E < 0.04 \quad (3'')$$

In addition, in this embodiment, it is preferable that the following conditional expressions (4') and (5') be satisfied instead of conditional expressions (4) and (5), and it is further preferable that conditional expressions (4") and (5") be satisfied.

$$1.55 < n_1 < 1.75 \quad (4')$$

$$1.55 < n_2 < 1.75 \quad (5')$$

$$1.6 < n_1 < 1.71 \quad (4'')$$

$$1.6 < n_2 < 1.71 \quad (5'')$$

In addition, in this embodiment, it is preferable that the following conditional expressions (6') and (7') be satisfied instead of conditional expressions (6) and (7), and it is further preferable that conditional expressions (6") and (7") be satisfied.

$$13 < \nu_1 < 45 \quad (6')$$

$$13 < \nu_2 < 45 \quad (7')$$

$$15 < \nu_1 < 40 \quad (6'')$$

$$15 < \nu_2 < 40 \quad (7'')$$

In addition, in this embodiment, it is preferable that the following conditional expression (9') be satisfied instead of conditional expression (9), and it is further preferable that conditional expression (9") be satisfied.

$$0.0005 < |n_1 - n_2| < 0.2 \quad (9')$$

$$0.001 < |n_1 - n_2| < 0.1 \quad (9'')$$

In addition, in this embodiment, it is preferable that the following conditional expression (10') be satisfied instead of conditional expression (10), and it is further preferable that conditional expression (10") be satisfied.

$$0.5<|v_1-v_2|<20 \tag{10'}$$

$$1<|v_1-v_2|<15 \tag{10''}$$

Furthermore, when employing the diffractive optical element 1 according to this embodiment in an endoscope, it is preferable that the relationship of conditional expression (11) be satisfied by the pixel pitch ccd_pitch of an image acquisition element provided in the endoscope and the depth $M_1$ of the relief pattern 4 in the diffractive optical element 1.

$$0.1<M_1/ccd\_pitch<200 \tag{11}$$

By satisfying conditional expression (11), an advantage is afforded in that the depth $M_1$ of the relief pattern 4 can be controlled within an appropriate range, and the processability can be enhanced.

Figure 2:
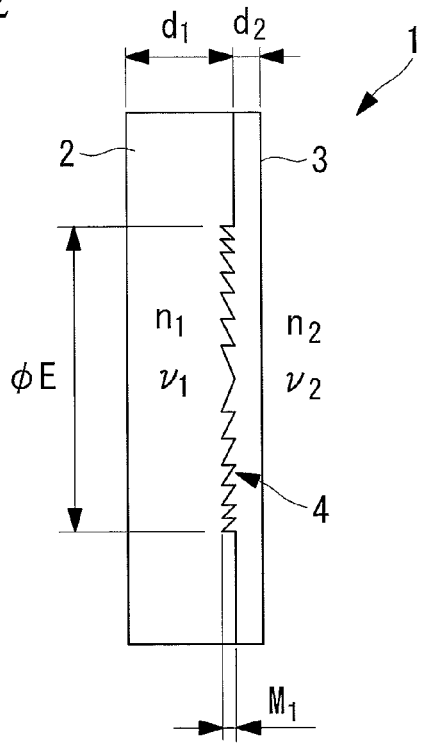
FIG. 2 is a longitudinal sectional view showing a first Example of the diffractive optical element in FIG. 1.

Next, a first Example of the diffractive optical element according to this embodiment will be described with reference to FIG. 2.

The diffractive optical element 1 according to this Example employs an energy-cured resin called "MR-7" made by Mitsui Chemicals as the first optical material layer 2, and an energy-cured resin called "UV-1000" made by Mitsubishi Chemical as the second optical material layer 3.

For these energy-cured resins, the refractive indices are $n_2=1.67$ and $n_2=1.64$, and the Abbe numbers are $v_1=31$ and $v_2=23$.

In addition, for these optical material layers 2 and 3, the center plate thicknesses are $d_1=0.9$ mm and $d_2=0.1$ mm; the effective diameter $\phi E$ of the relief pattern 4 is 3.0 mm; and the depth $M_1$ thereof is 0.0142 mm.

Figure 3:
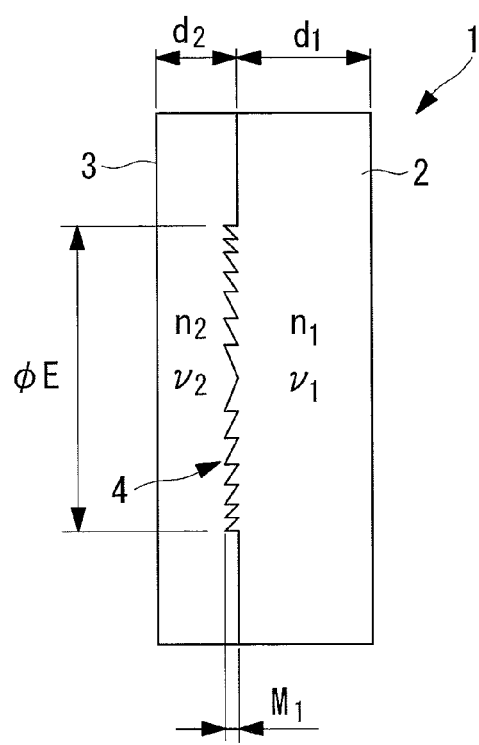
FIG. 3 is a longitudinal sectional view showing a second Example of the diffractive optical element in FIG. 1.

Next, a second Example of the diffractive optical element 1 according to this embodiment will be described with reference to FIG. 3.

The diffractive optical element 1 according to this Example employs an energy-cured resin called "MIU-L2000" made by MGC as the first optical material layer 2, and an energy-cured resin called "EP-5000" made by MGC as the second optical material layer 3.

For these energy-cured resins, the refractive indices are $n_2=1.63$ and $n_2=1.70$, and the Abbe numbers are $v_1=24$ and $v_2=35$.

In addition, for these optical material layers 2 and 3, the center plate thicknesses are $d_1=1.0$ mm and $d_2=0.06$ mm; the effective diameter $\phi E$ of the relief pattern 4 is 2.6 mm; and the depth $M_1$ thereof is 0.008 mm.

Figure 4:
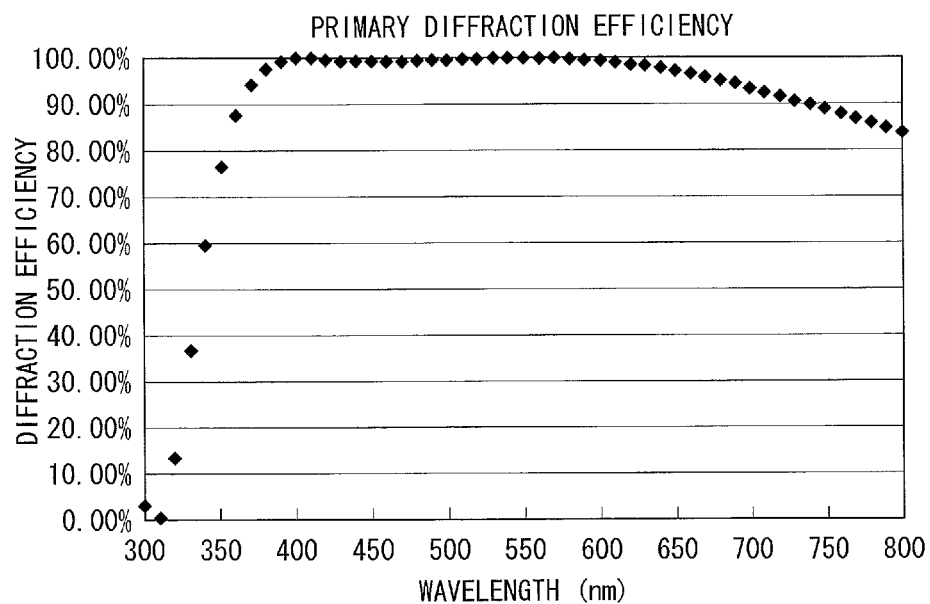
FIG. 4 is a diagram showing a graph of wavelength characteristic of diffraction efficiency for the first Example of the diffractive optical element in FIG. 1.
Figure 5:
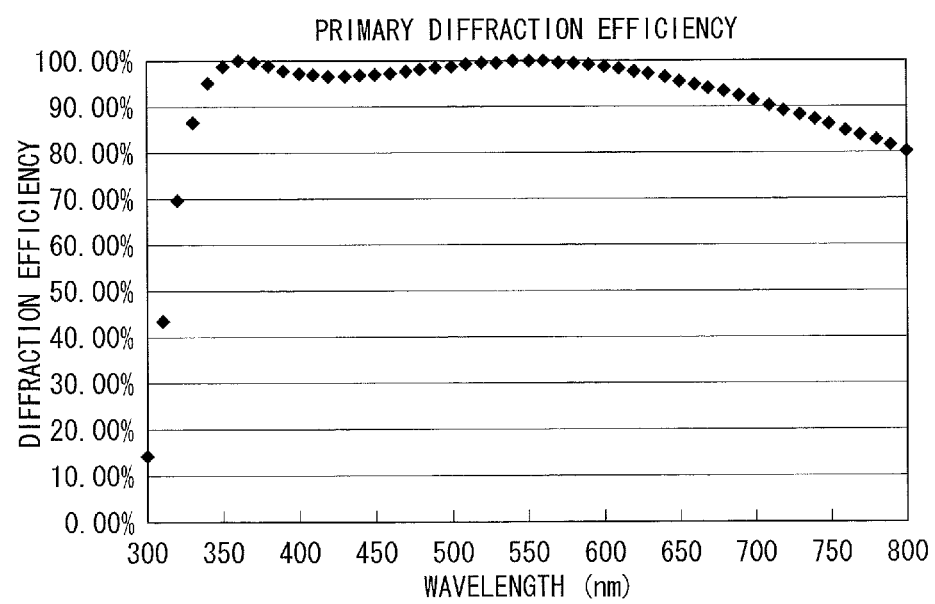
FIG. 5 is a diagram showing a graph of wavelength characteristic of diffraction efficiency for the second Example of the diffractive optical element in FIG. 1.

FIG. 4 shows the wavelength characteristic of diffraction efficiency for the diffractive optical element 1 of the first Example (Example 1). In addition, FIG. 5 shows the wavelength characteristic of diffraction efficiency for the diffractive optical element 1 of the second Example (Example 2). According to these figures, in both cases, a diffraction efficiency of 75% or greater is maintained in a wavelength range between 400 nm and 700 nm. Accordingly, there is an advantage in that the wavelength dependency of the diffraction efficiency is reduced, and flare can be decreased even if it is installed in an endoscope (flexible scope or rigid scope, not shown).

Furthermore, Table 1 shows individual coefficients and values obtained when applied to conditional expressions (1) to (11), for Example 1 and Example 2. According to Table 1, the diffractive optical elements of Example 1 and Example 2 both satisfy all of conditional expressions (1) to (11).

TABLE 1

| CONDITIONAL EXPRESSION | EXAMPLE 1 | EXAMPLE 2 | NOTE |
|---|---|---|---|
| (1) | 0.11 | 0.06 | |
| (2) | 0.30 | 0.38 | |
| (3) | 0.033 | 0.023 | |
| (4) | 1.67 | 1.63 | |
| (5) | 1.64 | 1.70 | |
| (6) | 31 | 24 | |
| (7) | 23 | 35 | |
| (8) | 1 | 1 | |
| (9) | 0.04 | 0.07 | |
| (10) | 8 | 11 | |
| (11) | 6.75 | 4.57 | |
| $d_1$ | 0.90 | 1.00 | ←mm |
| $d_2$ | 0.10 | 0.06 | ←mm |
| $\phi E$ | 3.0 | 2.6 | ←mm |
| $n_1$ | 1.67 | 1.63 | |
| $n_2$ | 1.64 | 1.70 | |
| $v_1$ | 31 | 24 | |
| $v_2$ | 23 | 35 | |
| $M_1$ | 14.2 | 8.0 | ←μm |
| ccd_pitch | 2.1 | 1.75 | ←μm |

REFERENCE SIGNS LIST 1 diffractive optical element
2 first optical material layer (optical material layer)
3 second optical material layer (optical material layer)
4 relief pattern

The invention claimed is:

1. A diffractive optical element that is formed by laminating two optical material layers formed of different energy-cured resins;
   in which a relief pattern is formed at an interface between the two optical material layers; and
   that satisfies the following conditional expressions:

$$0.01<d_2/d_1<0.2 \tag{1}$$

$$0.05<d_1/\phi E<1.0 \tag{2}$$

$$0.0005<d_2/\phi E<0.1 \tag{3}$$

wherein
$d_2$ is the center plate thickness (mm) of one optical material layer that is cured first,
$d_2$ is the center plate thickness (mm) of the other optical material layer that is cured later, and
$\phi E$ is the effective diameter (mm).

2. A diffractive optical element according to claim 1, which satisfies the following conditional expressions:

$$0.03<d_2/d_1<0.15 \tag{1'}$$

$$0.07<d_1/\phi E<0.6 \tag{2'}$$

$$0.0007<d_2/\phi E<0.06 \tag{3'}$$

3. A diffractive optical element according to claim 1, which satisfies the following conditional expressions:

$$0.05<d_2/d_1<0.12 \tag{1''}$$

$$0.1<d_1/\phi E<0.4 \tag{2''}$$

$$0.001<d_2/\phi E<0.04 \tag{3''}$$

4. A diffractive optical element according to claim 1, which satisfies the following conditional expressions:

$$1.5<n_1<1.8 \tag{4}$$

$$1.5<n_2<1.8 \tag{5}$$

wherein $n_1$ is the refractive index of the one optical material layer at the d-line, and $n_2$ is the refractive index of the other optical material layer at the d-line.

5. A diffractive optical element according to claim 4, which satisfies the following conditional expressions:

$$1.55 < n_1 < 1.75 \quad (4')$$

$$1.55 < n_2 < 1.75 \quad (5').$$

6. A diffractive optical element according to claim 4, which satisfies the following conditional expressions:

$$1.6 < n_1 < 1.71 \quad (4'')$$

$$1.6 < n_2 < 1.71 \quad (5'').$$

7. A diffractive optical element according to claim 1, which satisfies the following conditional expressions:

$$10 < v_1 < 50 \quad (6)$$

$$10 < v_2 < 50 \quad (7)$$

wherein $v_1$ is the Abbe number for the one optical material layer, and $v_2$ is the Abbe number for the other optical material layer.

8. A diffractive optical element according to claim 1, which satisfies the following conditional expressions:

$$13 < v_1 < 45 \quad (6')$$

$$13 < v_2 < 45 \quad (7').$$

9. A diffractive optical element according to claim 1, which satisfies the following conditional expressions:

$$15 < v_1 < 40 \quad (6'')$$

$$15 < v_2 < 40 \quad (7'').$$

10. A diffractive optical element according to claim 1, wherein, for the relief pattern, the pitch thereof gradually decreases toward peripheries thereof from the center of the optical material layers; the groove depth is uniform over the entirety thereof; and the following conditional expression is satisfied:

$$0.8 < M_1 \times |n_1 - n_2|/\lambda d < 1.2 \quad (8)$$

wherein $M_1$ is the groove depth of the relief pattern, $n_1$ is the refractive index of the one optical material layer at the d-line, $n_2$ is the refractive index of the other optical material layer at the d-line, and $\lambda d$ is the wavelength at the d-line.

11. A diffractive optical element according to claim 1, which satisfies the following conditional expression:

$$0.0001 < |n_1 - n_2| < 0.4 \quad (9)$$

wherein $n_1$ is the refractive index of the one optical material layer at the d-line, and $n_2$ is the refractive index of the other optical material layer at the d-line.

12. A diffractive optical element according to claim 11, which satisfies the following conditional expression:

$$0.0005 < |n_1 - n_2| < 0.2 \quad (9').$$

13. A diffractive optical element according to claim 11, which satisfies the following conditional expression:

$$0.001 < |n_1 - n_2| < 0.1 \quad (9'').$$

14. A diffractive optical element according to claim 1, which satisfies the following conditional expression:

$$0 < |v_1 - v_2| < 30 \quad (10)$$

wherein $v_1$ is the Abbe number for the one optical material layer, and $v_2$ is the Abbe number for the other optical material layer.

15. A diffractive optical element according to claim 14, which satisfies the following conditional expression:

$$0.5 < |v_1 - v_2| < 20 \quad (10').$$

16. A diffractive optical element according to claim 14, which satisfies the following conditional expression:

$$1 < |v_1 - v_2| < 15 \quad (10'').$$

17. A diffractive optical element according to claim 1, wherein the diffraction efficiency for first-order diffracted beams is 75% or greater in a wavelength range between 400 nm and 700 nm.

18. A diffractive optical element according to claim 1, wherein the optical material layers are UV-cured resins, heat-cured resins, or thermoplastic resins.

19. An endoscope provided with a diffractive optical element according to claim 1.

20. An endoscope according to claim 19 that is provided with an image acquisition element for capturing light transmitted through the diffractive optical element, and that satisfies the following conditional expression:

$$0.1 < M_1/ccd\_pitch < 200 \quad (11)$$

wherein $M_1$ is the groove depth of the relief pattern, and ccd_pitch is the pixel pitch of the image acquisition element.

* * * * *